(12) United States Patent
Wenzler et al.

(10) Patent No.: US 7,655,020 B2
(45) Date of Patent: Feb. 2, 2010

(54) SURGICAL PUNCHING INSTRUMENT

(75) Inventors: Jörg Wenzler, Hausen ob Verena (DE); Christoph Zepf, Silcherstrasse 8, 78589 Dürbheim (DE)

(73) Assignees: Jörg Wenzler Medizintechnik GmbH, Hausen ob Verena (DE); Christoph Zepf, Dürbheim (DE)

( * ) Notice: Subject to any disclaimer, the term of this patent is extended or adjusted under 35 U.S.C. 154(b) by 547 days.

(21) Appl. No.: 11/281,131

(22) Filed: Nov. 17, 2005

(65) Prior Publication Data

US 2006/0111737 A1 May 25, 2006

(51) Int. Cl.
*A61B 17/00* (2006.01)
(52) U.S. Cl. .......................... 606/185; 606/83
(58) Field of Classification Search ............ 606/83, 606/142, 143, 184, 185, 566, 567
See application file for complete search history.

(56) References Cited

U.S. PATENT DOCUMENTS

| | | | | | |
|---|---|---|---|---|---|
| 2,675,003 | A | * | 4/1954 | Veley | 606/173 |
| 3,752,161 | A | * | 8/1973 | Bent | 606/184 |
| 4,201,213 | A | * | 5/1980 | Townsend | 606/174 |
| 4,962,770 | A | * | 10/1990 | Agee et al. | 128/898 |
| 4,963,147 | A | * | 10/1990 | Agee et al. | 606/170 |
| 5,026,375 | A | | 6/1991 | Linovitz et al. | |
| 5,089,000 | A | * | 2/1992 | Agee et al. | 606/170 |

(Continued)

FOREIGN PATENT DOCUMENTS

DE 43 16 769 5/1994

(Continued)

*Primary Examiner*—Anhtuan T Nguyen
*Assistant Examiner*—Lian Huang
(74) *Attorney, Agent, or Firm*—McGlew and Tuttle, P.C.

(57) ABSTRACT

A surgical punching instrument is provided with a fixed handle (14) attached to a punching bar (2) and with an actuating lever (16), which is mounted thereon in a pivotingly movable manner and which is connected via a short lever arm (17) to a punching slide (1), which is in turn under the action of a restoring spring (23). The punching slide (1) lies with its flat sliding surface (3) on a flat guiding surface (4) of the punching bar (2) over its entire length and is guided at same in an axially movable manner by means of guide elements (5 through 8), which have a T-shaped profile, engage one another in a positive-locking manner and are detachable by longitudinal displacement. To make it possible to remove the restoring spring, which is not arranged between the handle and the actuating lever, from the punching bar in a simple manner, for example, for cleaning purposes, and to bring it into connection with same again, the restoring spring (23), designed as a compression coil spring, is arranged and guided at least partially in a guide groove (24) of the sliding surface of the punching slide (1) by means of a guide shaft (22, 22/1), which passes axially through it. A distal stop face (27), which is rigidly connected to the punching slide (1), is provided as a step bearing for the rear spring end of the restoring spring (23), and the restoring spring (23) is in contact by its front end with a proximal stop face (30) of the punching slide (1) when the punching slide (1) is removed, and with a proximal stop face (26) of the punching bar (2) when the punching slide (1) is mounted ready for operation.

20 Claims, 3 Drawing Sheets

U.S. PATENT DOCUMENTS

| | | | |
|---|---|---|---|
| 5,273,519 A * | 12/1993 | Koros et al. | 606/83 |
| 5,327,896 A * | 7/1994 | Schmieding | 600/566 |
| 5,449,365 A * | 9/1995 | Green et al. | 606/142 |
| 5,562,655 A * | 10/1996 | Mittelstadt et al. | 606/1 |
| 5,569,258 A | 10/1996 | Gambale | |
| 5,582,616 A * | 12/1996 | Bolduc et al. | 606/143 |
| 5,584,844 A | 12/1996 | Weisshaupt | |
| 5,800,362 A * | 9/1998 | Kobren et al. | 600/564 |
| 5,824,008 A * | 10/1998 | Bolduc et al. | 606/143 |
| 5,873,886 A * | 2/1999 | Larsen et al. | 606/180 |
| 5,964,772 A * | 10/1999 | Bolduc et al. | 606/142 |
| 6,083,177 A * | 7/2000 | Kobren et al. | 600/564 |
| 6,322,579 B1 * | 11/2001 | Muller | 606/205 |
| 6,562,051 B1 * | 5/2003 | Bolduc et al. | 606/143 |
| 7,169,156 B2 * | 1/2007 | Hart | 606/144 |
| 7,189,207 B2 * | 3/2007 | Viola | 600/564 |
| 2004/0049227 A1 * | 3/2004 | Jervis | 606/213 |
| 2004/0153101 A1 * | 8/2004 | Bolduc et al. | 606/143 |
| 2006/0085021 A1 * | 4/2006 | Wenzler | 606/184 |
| 2006/0155210 A1 * | 7/2006 | Beckman et al. | 600/567 |

FOREIGN PATENT DOCUMENTS

| | | |
|---|---|---|
| DE | 43 16 768 | 11/1994 |
| DE | 295 00 422.3 | 6/1995 |
| WO | WO 96/39959 | 12/1996 |

* cited by examiner

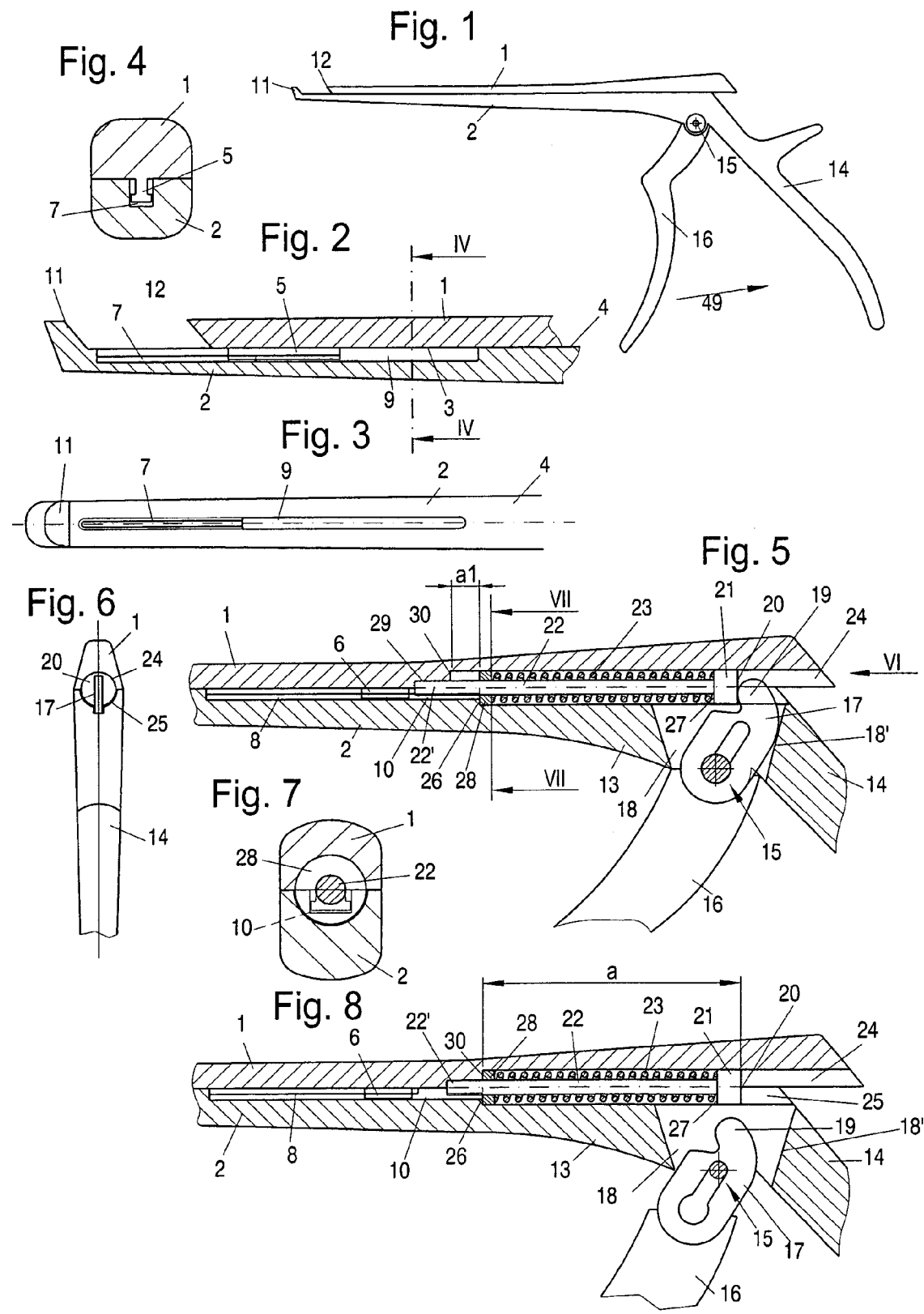

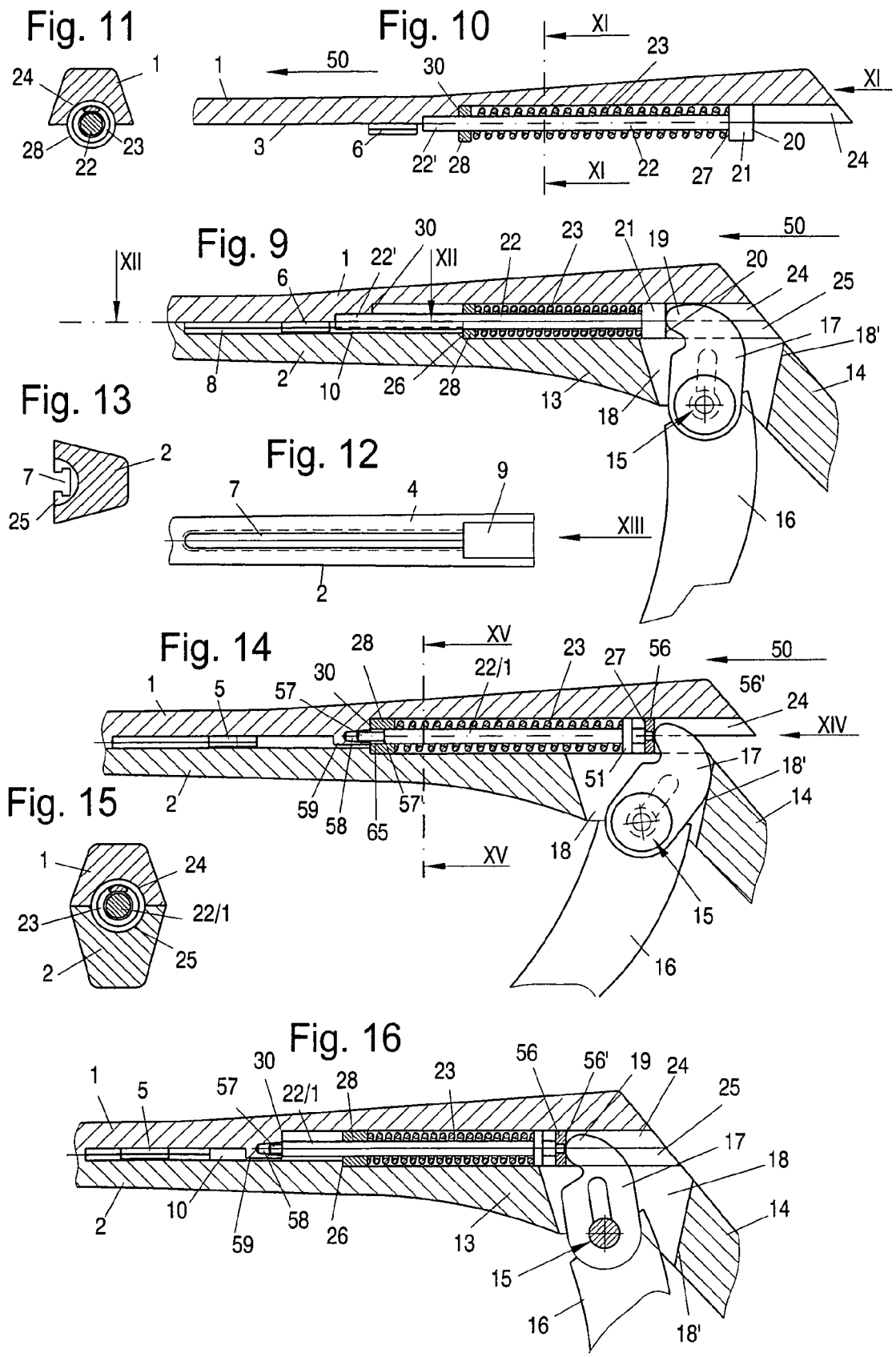

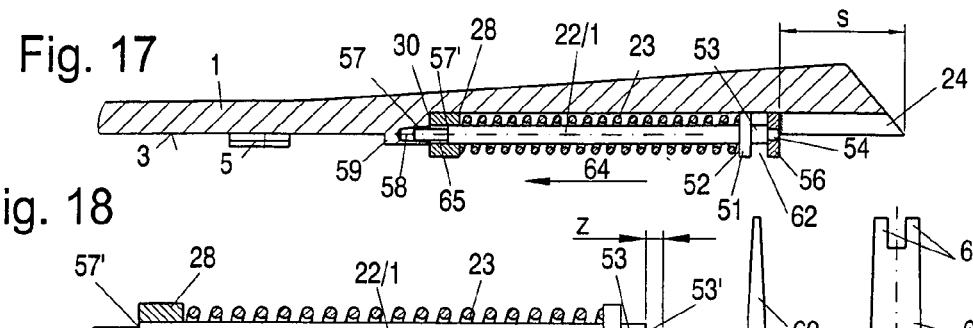
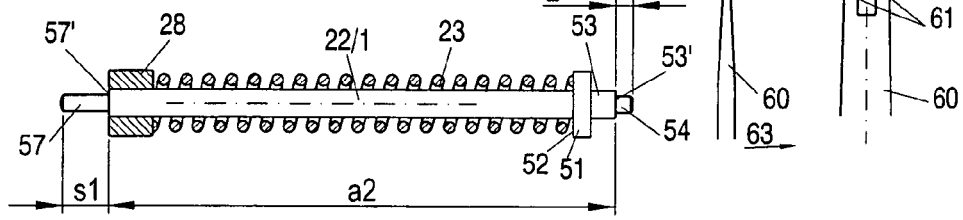
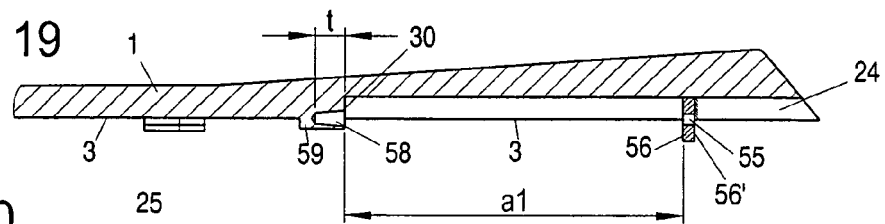
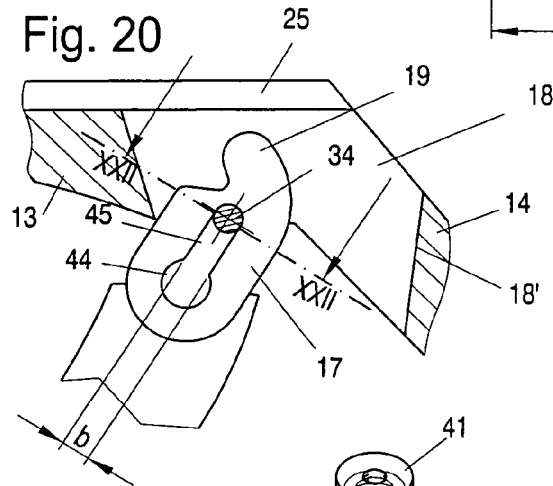
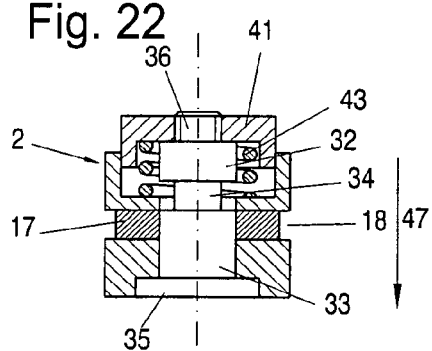
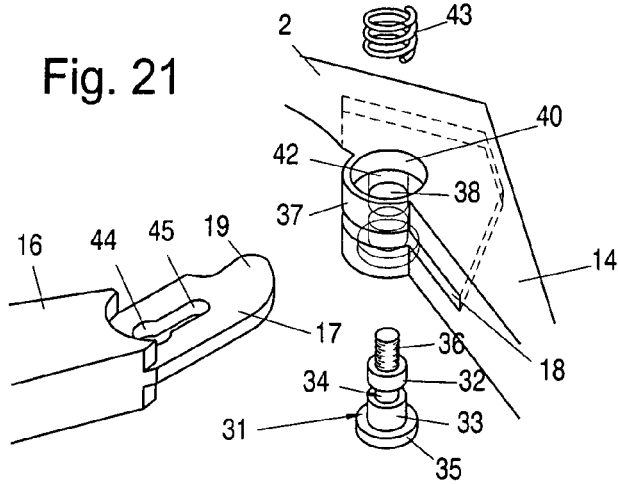
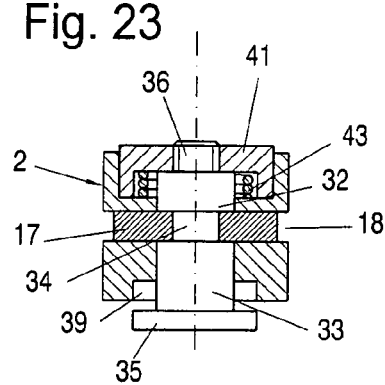

SURGICAL PUNCHING INSTRUMENT

CROSS REFERENCE TO RELATED APPLICATIONS

This application claims the benefit of priority under 35 U.S.C. § 119 of German Patent Application DE 20 2004 017 974.1 filed Nov. 19, 2004, the entire contents of which are incorporated herein by reference.

FIELD OF THE INVENTION

The present invention pertains to a surgical punching instrument with a fixed handle attached to a punching bar and with an actuating lever, which is mounted therein in a pivotably movable manner and which is in connection via a short lever arm with a punching slide, which is in turn under the effect of a restoring spring, wherein the punching slide lies with a flat sliding surface over its entire length on a flat guiding surface of the punching bar and is guided axially movably at the punching bar by means of guide elements, which are profiled in a T-shaped manner, engage one another in a positive-locking manner and are detachable by longitudinal displacement.

BACKGROUND OF THE INVENTION

Numerous variants of surgical punching instruments of this type have been known, for example, from the following documents: DE 43 16 768 A1, DE 43 16 769 C1, DE 295 00 422 U1, U.S. Pat. No. 5,026,375, U.S. Pat. No. 5,273,519, U.S. Pat. No. 5,569,258, and WO 96/39 959.

The restoring springs in the form of leaf springs are arranged in the prior-art punching instruments between the grip parts of the handle, on the one hand, and of the actuating lever, on the other hand, and are each attached to these at one end.

Aside from the fact that mounting or removal is difficult especially in case of prior-art restoring springs of a two-part design, such restoring springs may make the handling of the punching instruments difficult due to the fact that these springs fatigue or fail to apply the necessary restoring force to guarantee satisfactory functioning of the punching instrument.

In addition, these prior-art restoring springs cannot be readily removed from one another or from the particular grip part to which they are attached.

Even though surgical punching instruments have already been known (inhouse publication of Jörg Wenzler Medizintechnik GmbH) in which the two punch shafts, namely, the punching bar and the punching slide, are guided together in a tubular guide element of the grip part, the mobile punching slide is provided with a restoring spring, which is designed as a coil spring and is arranged between two axial stop faces on a guide shaft connected to the punching slide. In this prior-art surgical punching instrument, which is called a laminectomy punch, the rear end of the punching slides is provided with a cylindrical mounting part, which has on its front side a ring-shaped stop shoulder, by which the mounting part is in contact with an inner axial stop of the tubular guide part, which said axial stop is designed as a ring shoulder. The guide shaft, on which the restoring spring is arranged, is mounted axially displaceably in this mounting part. Via a short lever arm, the actuating lever is in functional connection with a rear-side pressing surface of the guide shaft of the restoring spring.

The two punch shafts can be removed only together from the guide part rigidly connected to the grip part in this prior-art laminectomy punch by being pulled together out of this on the rear side, after the short lever arm of the actuating lever has been removed from the cavity of the guide part. This short lever arm is mounted for this purpose together with the actuating lever in a radially displaceable manner on a pivot pin, which in turn has two sections with different diameters, which can be caused alternatingly to engage a larger hole and a narrower elongated hole against spring pressure.

The punching slide can only be removed from the punching bar when both are removed from the grip part. However, the punching bar is rigidly and nondetachably connected to the grip part in the surgical punching instrument of this class.

SUMMARY OF THE INVENTION

The basic object of the present invention is to provide a surgical punching instrument of the type described in the introduction, in which the restoring spring is not arranged between the handle and the actuating lever and can be removed from the punching bar and reconnected to same in a simple manner, for example, for cleaning purposes.

This object is accomplished according to the present invention by the restoring spring designed as a compression coil spring being arranged and guided at least partially in a guide groove of the sliding surface of the punching slide by means of a guide shaft passing axially through it, wherein a distal stop face rigidly connected to the punching slide is provided as the step bearing for the rear spring end of the restoring spring and the restoring spring is in contact by its front end with a proximal stop face of the punching slide with the punching slide removed and is in contact with a proximal stop face of the punching bar in the state in which the punching slide is mounted ready for operation.

Due to the design of the surgical punching instrument according to the present invention, a plurality of advantages are obtained compared to the conventional punching instruments of the type of this type.

Even the use of a restoring spring designed as a compression coil spring and the arrangement thereof in a guide groove of the punching slide offers the advantage that the restoring spring acts directly on the punching slide and that the particular resetting can be guaranteed as a result with a substantially higher level of reliability when the actuating lever is released. In addition, the restoring spring can be removed from the punching bar together with the punching slide, so that the cleaning of the entire device is substantially facilitated. The attachment of the punching slide to the punching bar together with the restoring spring for correct operation is advantageously simplified as well.

Due to an embodiment according to another aspect of the invention, an increase in the reliability of operation and facilitation of the attachment of the punching slide to the punching bar are achieved insofar as the spring can be brought into contact with and supported at the stop faces in a reliable manner due to the thrust collar provided.

While the embodiments according to another aspect of the invention lead above all to advantages in terms of manufacturing technology and to space-saving arrangement of the restoring spring, while another aspect leads, in a simple manner, to a rigid connection between the restoring spring and the punching slide, which connection makes possible very simple handling in terms of the disassembly and the assembly of the punch shafts.

It is advantageous concerning the reliability of operation to rigidly weld the guide shaft to the proximal end of the longitudinal groove of the punching slide in a depression corresponding to half of its diameter and to thus connect it rigidly at both ends to the punching slide.

However, it is also possible due to the embodiment according to another aspect of the invention to attach the guide shaft together with the restoring spring guided thereon detachably to the punching slide. The guide shaft with the restoring spring can be removed from the punching slide in a simple manner and can again be inserted into same in an equally simple manner in this embodiment, which is of great advantage especially for cleaning purposes. In addition, the restoring spring can be easily replaced when needed.

Due to the embodiment according to another aspect of the invention, it is achieved that the guide shaft can be attached and the necessary pressing surface can be arranged for the actuation of the punching slide in a reliable manner, on the one hand, and in a simple manner in terms of manufacturing technology, on the other hand.

Due to the embodiments according to another aspect of the invention, the separation of the guide shaft from the guide groove of the punching slide and the reinsertion of the guide shaft become so simple that these operations can easily be carried out even by unskilled persons.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a reduced scale side view of a surgical punching instrument;

FIG. 2 is an enlarged scale view of the proximal (front) sections of the two punch shafts;

FIG. 3 is a top view of the front section of the punching bar;

FIG. 4 is a sectional view of section IV-IV from FIG. 2;

FIG. 5 is an enlarged sectional view of the rear section of the punching instrument shown in FIG. 1 in the non-actuated inoperative position of the punching slide;

FIG. 6 is a rear front view VI from FIG. 5;

FIG. 7 is a sectional view of a section VII-VII from FIG. 5;

FIG. 8 is the same parts as FIG. 5, but in another functional position of the actuating lever;

FIG. 9 is the same parts as FIG. 5 in the actuated closed position of the punching slide;

FIG. 10 is a sectional view of the rear part of the punching slide removed from the punching bar;

FIG. 11 is a rear front view XI from FIG. 10;

FIG. 12 is a partial sectional view of a section XII-XII from FIG. 9;

FIG. 13 is the rear front view XIII from FIG. 12;

FIG. 14 is the rear part of another embodiment of the surgical punching instrument in a sectional view and in the non-actuated inoperative position of the punching slide;

FIG. 15 is a rear front view XV from FIG. 14;

FIG. 16 is the same parts as FIG. 14, but in the actuated closed position of the punching slide;

FIG. 17 is the rear part of the punching slide from FIGS. 14 and 16, which is removed from the punching bar;

FIG. 18 is the guide shaft with the restoring spring and the thrust collar as an individual part;

FIG. 19 is the rear part of the removed punching slide without guide shaft and restoring spring;

FIG. 20 is an enlarged sectional view of the mounting of the actuating lever in the released position shown in FIG. 8;

FIG. 21 is an isometric exploded view of the individual parts of the mounting of the actuating lever;

FIG. 22 is a sectional view of a section XXII-XXII from FIG. 20 in a released position of the short lever arm; and FIG. 23 is the same sectional view as FIG. 22, but in the normal operating position of the short lever arm and of the actuating lever.

DESCRIPTION OF THE PREFERRED EMBODIMENTS

Referring to the drawings in particular, the instrument shown in the drawings is a laminectomy punch with two punch shafts, namely, a punching slide 1 and a punching bar 2. These two punch shafts have U-shaped cross-sectional profiles each, the mobile punching slide 1 lying on a flat guiding surface 4 of the punching bar with a flat sliding surface 3 extending over the entire length. The punching slide 1 is movably connected to the punching bar 2 by two guide beads 5 and 6, which have a T-shaped profile and project from the sliding surface 3 on the underside at spaced locations from one another. To receive these guide beads 5 and 6, the punching bar 2 is provided in its guiding surface 4 with guide grooves 7 and 8 having a T-shaped profile, which are joined by widened lead-in grooves 9 and 10 and from which they can be removed. The punching slide 1 is thus detachably connected to the punching bar 2.

The front end of the punching bar 2 is provided with an upwardly directed punching foot 11, which acts as an abutment for the front-side punching edge 12 of the punching slide 1.

The rear end 13 of the punching bar 2 is provided with a grip part 14, which is connected to it in one piece and at which an actuating lever 16 is pivotably mounted by means of a special pivot pin 15. This actuating lever 16 has a short lever arm 17, which is accommodated in a slot-like opening 18 of the punching bar 2 in a pivotingly movable manner. With a rounded pressing finger 19, the short lever arm 17 is in contact, for actuating the punching slide 1, with a pressing surface 20, which is formed by the rear front surface of a cylindrical head part 21 of a guide shaft 22. The guide shaft 22 has a diameter that is about half that of the head part 21 and acts as a guide element for a restoring spring 23, which is designed as a compression coil spring. The head part 21 of the guide shaft 22 is attached, namely, rigidly welded, in a semicylindrical guide groove 24 of the punching slide 1, which said guide groove 24 is open on the rear side, so that the head part 21 projects with half of its diameter from this guide groove 24.

To receive this projecting half diameter of the head part 21, a likewise semicylindrical longitudinal groove 25, which is complemented by the guide groove 24 to form a cylindrical hole, is milled into the guiding surface 4 of the punching bar 2. This longitudinal groove 25, which is likewise open on the rear side, ends at a proximal stop face 26 of the punching slide, which said stop face acts as a stop for the front end of the restoring spring 23. The annular surface 27 of the head part 21, which said head part is rigidly connected to the punching slide 1 by welding, is provided as a step bearing (distal stop face) for the rear spring end of the restoring spring 23. To guarantee a better engaging position between the front end of the restoring spring 23 and the stop face 26, a thrust collar 28, which is fittingly in contact with the stop face 26, is arranged on the guide shaft 22 in an axially movable manner.

The front end 22' of the guide shaft 22 projects by half of its diameter into a semicylindrical opening 29 and is welded therein.

The guide groove 24 ends at a semicircular stop face 30. The distance a between this stop face 30 and the pressing surface 20 of the head part 21 is selected here to be such that the restoring spring 23 has a certain pretension in the inoperative or starting position of the punching slide 1 and is thus certainly able to return the punching slide 1 completely into its starting position. This starting position is defined by the short lever arm 17 being in contact with the rear limiting surface 18' of the opening 18, in which the short lever arm 17 is arranged in a pivotingly movable manner (FIG. 5 and FIG. 14).

It is recognized from FIG. 5 that there is a distance a1, which is necessary for generating the pretension of the restoring spring 23, between the stop face 30 of the punching slide 1 and the stop face 26 of the punching bar 2 in the inoperative position of the punching slide 1. With the punching slide 1 removed, the thrust collar 28 is in contact with this stop face 30 of the punching slide, as is shown in FIG. 10.

As is apparent from FIG. 9, the punching slide 1 is moved from the short lever arm 17 and the contact thereof with the head part 21 in the closing direction indicated by arrow 50 on corresponding actuation of the actuating lever 16 in the direction of arrow 49 and the punching edge 12 is thus displaced against the punching foot 11.

When the actuating lever 16 is again released, the punching slide 1 is returned by the restoring spring 23 into the inoperative position shown in FIGS. 1, 2 and 5.

In the inoperative position of the punching slide 1 shown in FIG. 5, the two guide beads 5 and 6 of the punching slide 1 still engage the T-shaped guide grooves 7 and 8 of the punching bar 2.

To make it possible to remove the punching slide 1 from the punching bar 2, it is necessary to remove the pressing finger 19 of the short lever arm 17 of the actuating lever 16 from the path of movement of the head part 21. To make this possible, a special mounting of the actuating lever 16 at the punching bar 2 is provided, which mounting will now be explained in greater detail on the basis of FIGS. 5, 8 as well as 20 through 23.

A bearing bolt 31, which has a core part 34 of reduced diameter between two cylindrical bearing sections 32 and 33, is provided for mounting the actuating lever 16. The bearing section 33 is provided with a head disk 35 of increased diameter, whereas the bearing section 32 is joined by a threaded pin 36.

A through bearing hole 38, whose diameter is coordinated with the diameter of the two bearing sections 32 and 33, is provided in a bearing eye 37 of the punching bar 2 to receive this bearing bolt 31. The lower end of this bearing hole 38 is provided with an expanded opening 39 for receiving the head disk 35, whereas the upper end has a cylindrical opening 40, which is used to receive a knurled nut 41 screwed onto the threaded pin 36. A compression spring 43, which secures the bearing bolt in the axial position shown in FIG. 22, is located between the knurled nut 41 and an annular surface 42 of the opening 40. In this axial position, the bearing section 33 of the bearing bolt 31 protrudes into a cylindrical hole 44 of the short lever arm 17, which said hole is joined by an elongated hole 45, whose width b is reduced on the diameter of the core part 34. It is thus ensured that the actuating lever 16 with its short lever arm 17 cannot be moved out of the path of movement of the head part 21 of the guide shaft 22 as long as the bearing section 33 of the bearing bolt 31 engages the hole 44.

To make it possible to bring the short lever arm 17 or the pressing finger 19 thereof from the path of movement of the head part 21 in the direction of arrow 46 into the position shown in FIGS. 8 and 20, it is necessary to bring about a displacement of the bearing bolt 31 in the direction of arrow 47 by pressing the knurled nut 41 screwed onto the threaded pin 36, so that the core part 34 will come to lie in the area of the short lever arm 17 and can be received by the elongated hole 45.

The short lever arm 17 can be pulled out of the opening 18 and consequently the path of movement of the head part 21 by the length of the elongated hole 45 in this position of the bearing bolt 31.

The punching slide 1 can be displaced in the direction of arrow 48 in this pulled-out position of the short lever arm 17 to the extent that the engaging elements 5 and 7 as well as 8 and 9 can be separated from one another and the punching slide 1 can be removed from the punching bar. When the punching slide 1 is removed from the punching bar 2, the thrust collar 28 is in contact with the stop face 30, as is shown in FIG. 10.

The attachment of the punching slide 1 to the punching bar 2 is likewise carried out with the short lever arm 17 pulled out. After the attachment of the punching slide 1 to the punching bar 2, during which the engaging elements 5 through 8 have been engaged with one another and the restoring spring 23 has been somewhat pretensioned, the short lever arm 17 is again pushed into its working position shown in FIG. 5. The compression spring 43 now causes the bearing part 33 of the bearing bolt 31 to engage the hole 44 again, and the readiness of the punching instrument to function is restored.

Even though the restoring spring 23 can be removed with the punching slide 1 from the punching bar 2 in the embodiment of the surgical punching instrument described so far, because the guide shaft 22 with its head part 21 and with its front end 22' is welded to the punching slide 1 and is thus rigidly connected, the compression spring 23 cannot be removed from the punching slide 1.

However, FIGS. 14 through 19 show an embodiment in which a guide shaft 22/1 and the restoring spring 23 arranged thereon can also be removed from the punching bar 1. At its rear, i.e., distal end, this guide shaft 22/1 has a ring disk 51, whose front, i.e., proximal face forms the stop face 52 for the restoring spring 23. A bearing bolt 54 is arranged at a distance bolt 53 of reduced diameter, which joins the ring disk 51 in one piece on the rear side. This bearing bolt 54 is mounted loosely in a central hole 55 of a bearing disk 56. It is held in this hole 55 by the restoring spring 23.

The bearing disk 56 has a diameter that is coordinated with the semicylindrical shape of the guide groove 24 of the punching slide 1. The bearing disk 56 is welded at a certain distance s from the rear end of the punching slide 1 into the guide groove 24, i.e., it is rigidly connected therewith, so that the axis of the bearing hole 55 is in the plane of the sliding surface 3. A bearing hole 58 for a front bearing bolt 57 of the guide shaft 22/1 is arranged in the stop face 30 coaxially with the bearing hole 55 of the bearing disk 56. To completely receive this bearing hole 58, a semicylindrical bulge 59, whose radius is, however, smaller than that of the thrust collar 28, is provided on the underside of the sliding surface 3. It may be advantageous for manufacture to provide for the bearing hole 58 a bearing bush, which is inserted, especially welded, into the guide groove 24, which is selected to be correspondingly longer than the cavity forming the bearing hole 58.

The depth t of the bearing hole 58 and the length of the bearing bolt 57 are selected here to be such that the bearing bolt 57 can be pushed into the bearing hole 58 by the length z of the rear bearing bolt 54 and the rear bearing bolt 54 can at the same time be pushed out of the bearing hole 55 of the bearing disk 56. However, it is also necessary for this that the axial distance a1 between the stop face 30 and the bearing disk 56 be greater by the length z of the rear bearing bolt 54 than the axial distance a2 between the rear front-side annular surface 53' of the distance bolt 53 and the front annular face 57' of the guide pin 22/1.

The thrust collar 28 has a greater width in this embodiment than in the embodiment according to FIGS. 5 through 10. This greater width is needed to bridge over the annular gap 65, which can be recognized in FIGS. 14 and 17 and is present between the stop face 30 and the annular surface 57' of the guide shaft 22/1, which said annular surface 57' surrounds the bearing bolt 57, when the guide shaft 22/1 is inserted into the punching slide 1.

While the removal of the punching slide 1 from the punching bar 2 is carried out in the same manner in this embodiment as in the above-described embodiment according to FIGS. 1 through 15, it is possible here to remove the punch shaft 22/1 and the restoring spring 23 from the punching slide 1. A screwdriver or a similar tool can be used for this purpose. However, it is more expedient to use a fork-shaped tool 60. The prongs 61 this fork-shaped tool are pushed into the intermediate space 62 present between the bearing disk 56 and the ring disk 51, and the bearing bolt 54 can be pushed out of the bearing hole 55 by corresponding pivoting in the direction of arrow 63 and removed from the guide groove 24 downwards.

To also make it now possible to pivot the guide shaft or the bearing bolt 57 thereof in the bearing hole 58, the bearing hole 58 is advantageously provided with a somewhat larger diameter than the bearing bolt 57 and/or has a conical design.

The punching bar 2 with its actuating lever 16 and with the short lever arm 17 have the same design as in the embodiment of the surgical punching instrument described first. The mode of operation is also the same.

The reinsertion of the guide shaft 22/1 with the compression spring and with the thrust collar 28 is carried out in such a way that the front bearing bolt 57 is first inserted into the expanded or conical bearing hole 58 of the punching slide 1 and the rear bearing bolt 54 is then inserted into the bearing hole 55 while correspondingly compressing the restoring spring 23. The restoring spring and the thrust collar 28 are, of course, already positioned on the guide shaft 22/1 in the manner shown in FIG. 18.

It is obvious that the thrust collar 28 and the restoring spring 23 can also be removed from the guide shaft 22/1.

While specific embodiments of the invention have been shown and described in detail to illustrate the application of the principles of the invention, it will be understood that the invention may be embodied otherwise without departing from such principles.

What is claimed is:

1. A surgical punching instrument, comprising:
    a punching bar, said punching bar having a punching bar groove at a distal end thereof;
    a fixed handle integrally attached to said punching bar;
    an actuating lever pivotably movably mounted on said handle;
    a punching slide having a punching slide groove at a distal end thereof, wherein said punching slide lies with a flat sliding surface over its entire length on a flat guiding surface of said punching bar and is guided at said punching bar in an axially movable manner by means of guide elements, said guide elements having a T-shaped profile, said guide elements detachably engaging one another in a positive-locking manner, said guide elements being detachable from one another via a longitudinal displacement such that said punching slide is removed from said punching bar in a detached state;
    a short lever arm connected to said actuating lever and connected to said punching slide;
    a restoring spring acting on said punching slide;
    a guide shaft, said punching bar groove and said punching slide groove defining a cavity when said punching slide is connected to said punching bar, said restoring spring being provided as a compression coil spring arranged and guided at least partially in said groove of said punching slide by means of said guide shaft passing through said restoring spring axially, said guide shaft being coaxially arranged with said guide groove of said punching slide, said guide shaft having a distal stop face rigidly connected to said punching slide, a rear spring end of said restoring spring bearing on said distal stop face, said punching bar having a proximal stop face and said punching slide having a proximal stop face, said restoring spring having a front end adjacent to said proximal stop face of said punching slide when said punching slide is removed, said spring being arranged in said cavity such that one portion of said spring is located in said groove of said punching slide and another portion of said spring is located in said groove of said punching bar when said punching slide is mounted to said punching bar, wherein a front end of said spring is opposite said proximal stop face of said punching bar and said proximal stop face of said punching bar when said punching bar is mounted to said punching slide, said short lever arm being in contact with said distal stop face when said punching slide is connected to said punching bar, said short lever arm not being in contact with said distal stop face when said punching slide is detached from said punching bar in said detached state.

2. A surgical punching instrument in accordance with claim 1, wherein a thrust collar movable on said guide shaft is arranged between a front end of the spring and said proximal stop faces.

3. A surgical punching instrument in accordance with claim 1, wherein said restoring spring is located with part of its diameter in said guide groove of said punching slide and with the remaining part of the diameter in a longitudinal groove of said guiding surface of said punching bar.

4. A surgical punching instrument in accordance with claim 1, wherein said guide groove of said punching slide and said longitudinal groove of said punching bar end each at one of said proximal stop faces.

5. A surgical punching instrument in accordance with claim 1, wherein said guide shaft is provided with a head part, which has said distal stop face for said restoring spring and a distal pressing surface of said punching slide, said head part having a diameter that is at least equal to a diameter of said restoring spring.

6. A surgical punching instrument in accordance with claim 5, wherein said head part of said guide shaft is stationarily welded into said guide groove of said punching slide and a front side of said head part facing away from said restoring spring forms said distal pressing surface.

7. A surgical punching instrument in accordance with claim 6, wherein said guide shaft is rigidly connected, by a proximal end section to said punching slide in the area of said proximal stop face.

8. A surgical punching instrument in accordance with claim 1, wherein said guide shaft is mounted detachably in two bearing holes of said punching slide, which are coaxial with one another, by means of said bearing bolts arranged at its ends.

9. A surgical punching instrument in accordance with claim 8, wherein both said bearing holes are located in the plane of said sliding surface, one said bearing hole being arranged in a semicylindrical bulge and said second bearing hole being arranged in a cylindrical bearing disk, which is attached, especially welded, in said guide groove of said punching slide and said distal face thereof forms said pressing surface for said short lever arm of said actuating lever.

10. A surgical punching instrument in accordance with claim 8, wherein said guide shaft has at its distal end a ring disk as a head part, at which said ring disk said restoring sprig is supported, and which is joined by a distance bolt, which has a smaller diameter, is provided with said bearing bolt and is in contact by its said ring-shaped face with said bearing disk forming said stop face.

11. A surgical punching instrument in accordance with claim 9, wherein said guide shaft is movable axially against said proximal stop face at least by the length of said bearing bolt mounted in said bearing disk.

12. A surgical punching instrument in accordance with claim 2, wherein said guide shaft is provided with a head part, which has said distal stop face for said restoring spring and a distal pressing surface of said punching slide, said head part having a diameter that is at least equal to a diameter of said restoring spring.

13. A surgical punching instrument in accordance with claim 2, wherein said guide shaft is provided with a head part, which has said distal stop face for said restoring spring and a distal pressing surface of said punching slide, said head part having a diameter that is at least equal to a diameter of said restoring spring.

14. A surgical punching instrument, comprising:
a punching bar with a fixed handle integrally connected thereto, said punching bar having a flat guiding surface and a defined punching bar groove, said punching bar having guiding elements and a punching bar proximal stop surface;
an actuating lever mounted on said handle such that said actuating lever pivots from a first lever position to a second lever position;
a punching slide having a flat sliding surface along an entire length thereof and a punching slide proximal stop surface, said punching slide having a defined punching slide groove, said punching slide having guide engaging elements, each guiding element of said punching bar receiving one of said guide engaging elements of said punching slide such that said punching slide is detachably connected to said punching bar when said punching bar and said punching slide are in a connected state, whereby said punching slide is detached from said punching bar via a longitudinal displacement, said punching slide being located at a spaced location from said punching bar when said punching bar and said punching slide are in a disconnected state, said flat sliding surface of said punching slide engaging said flat guiding surface of said punching bar in said connected state such that said punching slide is movable along said punching bar in an axial direction;
a lever arm connected to said actuating lever and said punching slide;
a restoring spring, said punching slide groove and said punching bar groove defining a receiving space when said punching bar and said sliding bar are in said connected state, wherein at least a portion of said restoring spring is located within said receiving space;
a guide shaft extending axially through said restoring spring, said guide shaft having a head part at one end thereof, said head part being fixed to said punching slide, said head part engaging one end of said restoring spring, said lever arm contacting said head part when said actuating lever is in said second position and when said punching bar and said punching slide are in said connected state such that said head part compresses said restoring spring, another end of said restoring spring being adjacent to said punching slide proximal stop surface when said punching bar and said punching slide are in said disconnected state, said another end of said restoring spring being adjacent to said punching bar proximal stop surface when said punching bar and said punching slide are in said connected state.

15. A surgical punching instrument in accordance with claim 14, wherein said restoring spring is in an uncompressed when said actuating lever is in said first position.

16. A surgical punching instrument in accordance with claim 14, wherein said lever arm is not in contact with said head part when said actuating lever is in said first lever position.

17. A surgical punching instrument in accordance with claim 14, further comprising a bearing bolt, said bearing bolt connecting said lever arm to said punching slide, wherein said lever arm has a hole and an elongated slot, said hole being in communication with said elongated slot, said bearing bolt being located in said hole when said actuating lever is in said second lever position and said punching slide and said punching bar are in said connected state, said bearing bolt being located in said elongated slot when said actuating lever is in said first lever position.

18. A surgical punching instrument, comprising:
a punching bar with a fixed handle integrally connected thereto, said punching bar having a flat guiding surface and a defined punching bar groove, said punching bar having guiding elements and a proximal stop surface;
an actuating lever mounted on said handle such that said actuating lever pivots from a first lever position to a second lever position;
a punching slide having a flat sliding surface along an entire length thereof, said punching slide having a defined punching slide groove, said punching slide having guide engaging elements, each guiding element of said punching bar receiving one of said guide engaging elements of said punching slide such that said punching slide is detachably connected to said punching bar, said flat sliding surface of said punching slide engaging said flat guiding surface of said punching bar such that said punching slide is movable along said punching bar in an axial direction;
a lever arm connected to said actuating lever and said punching slide;
a restoring spring, said punching slide groove and said punching bar groove defining a receiving space, wherein at least a portion of said restoring spring is located within said receiving space;
a thrust collar;
a guide shaft extending axially through said restoring spring and said thrust collar, said guide shaft having a head part at one end thereof, said head part being fixed to said punching slide, said head part engaging one end of said restoring spring, said thrust collar engaging another end of said restoring spring, said proximal stop surface of said punching bar engaging said thrust collar when said actuating lever is in said second position, said lever arm contacting said head part when said actuating lever is in said second position such that said head part compresses said restoring spring, said proximal stop surface of said punching slide being located at a spaced location from said thrust collar when said actuating lever is in said second position.

19. A surgical punching instrument in accordance with claim 18, further comprising a bearing bolt, said bearing bolt connecting said lever arm to said punching slide, wherein said lever arm has a hole in communication with an elongated slot, said bearing bolt being located in said hole when said actuating lever is in said second lever position, said bearing bolt being located in said elongated slot when said actuating lever is in said first lever position.

20. A surgical punching instrument in accordance with claim 18, wherein said restoring spring is in an uncompressed state when said actuating lever is in said first position.

* * * * *